United States Patent [19]

Jones

[11] Patent Number: 5,201,744
[45] Date of Patent: Apr. 13, 1993

[54] METHOD AND DEVICE FOR SUTURING USING A ROD WITH A NEEDLE HOLDER

[76] Inventor: Mark W. Jones, 841 Audubon St., East Lansing, Mich. 48823

[21] Appl. No.: 802,486

[22] Filed: Dec. 5, 1991

[51] Int. Cl.$^5$ .............................................. A61B 17/00
[52] U.S. Cl. .................................. 606/148; 606/139; 606/1
[58] Field of Search .................... 606/148, 139, 144, 1

[56] References Cited

U.S. PATENT DOCUMENTS

| | | | |
|---|---|---|---|
| 2,416,260 | 2/1947 | Karle | 606/144 |
| 2,689,147 | 9/1954 | Smalley | 606/144 |
| 2,895,478 | 7/1959 | Post | 606/144 |
| 3,871,379 | 3/1975 | Clarke | |
| 4,226,241 | 10/1980 | Walker, Jr. | 606/148 X |
| 4,462,395 | 7/1984 | Johnson | 606/75 |
| 4,597,390 | 7/1986 | Mulhollan et al. | 606/147 X |
| 4,602,635 | 7/1986 | Mulhollan et al. | 606/144 |
| 4,683,885 | 8/1987 | Hutterer et al. | 606/144 |
| 4,760,848 | 8/1988 | Hasson | 606/222 X |
| 4,935,027 | 6/1990 | Yoon | 606/148 X |

Primary Examiner—Stephen C. Pellegrino
Assistant Examiner—Jeffrey A. Schmidt
Attorney, Agent, or Firm—Ian C. McLeod

[57] ABSTRACT

A surgical knot tier instrument (10) for use in conjunction with a needle (29) connected to suture thread (13) and a pair of surgical forceps (31), for placing a knot (11) in a wound (15) in body tissue (17), is described. The knot tier instrument is comprised of an elongate rod member (19) having a relatively small circular cross-section along a longitudinal axis A—A of the rod. This allows the rod to be introduced into a body cavity through an entry puncture wound for helping a physician or surgeon to close the wound in the body tissue without having to completely open up the body cavity. A proximal, working end (21) of the rod is provided with a notch (25), formed diametrically across an end face (23) of the rod, and a slot (27), which is provided diametrically across the face, offset 90° from the notch. During the surgery procedure, the forceps are used to manipulate the needle connected to the suture thread to pull the needle with the suture thread through the wound. The slot in the rod which is magnetized then acts to receive and hold the needle to free up the forceps. The forceps can now be manipulated to regrasp the needle to form the knot in the suture thread. The notch is then mounted on the knot with the opposed ends of the suture thread extending from the opposed ends of the notch. The notch is used in conjunction with the forceps to tighten and center the suture on the wound. That way, the suture knot helps to draw the tissue on either side of the wound together in a uniform manner.

13 Claims, 2 Drawing Sheets

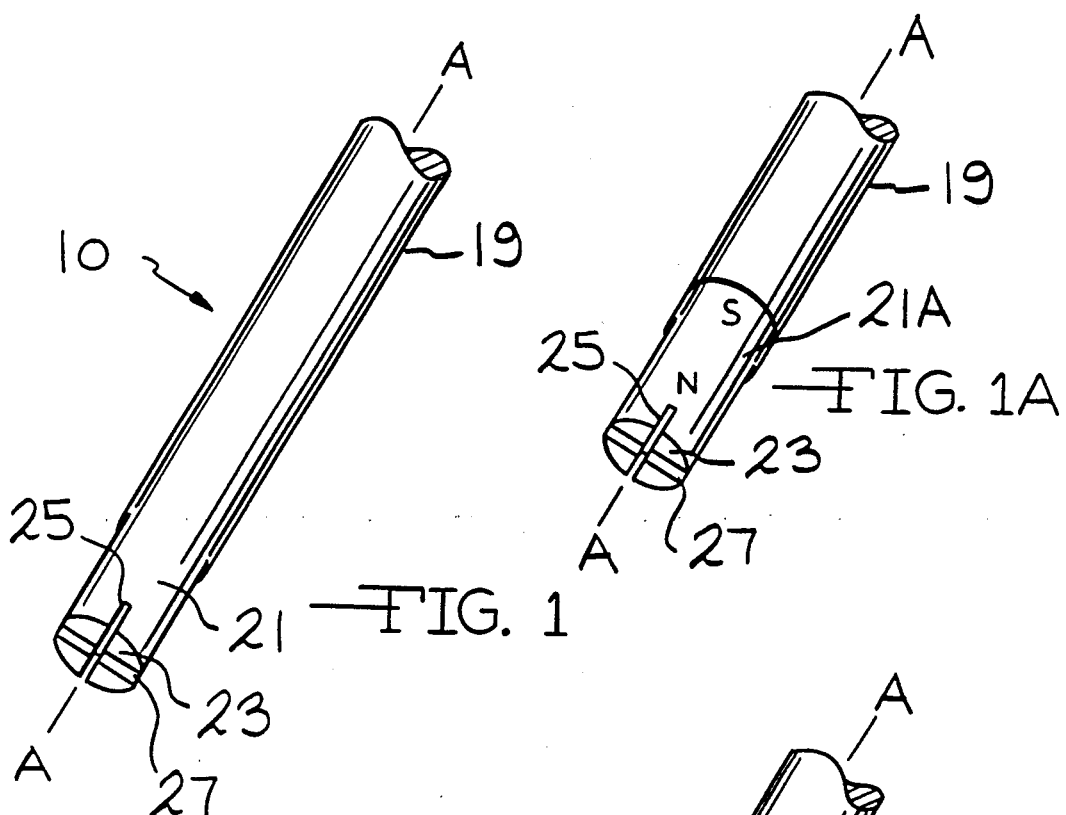
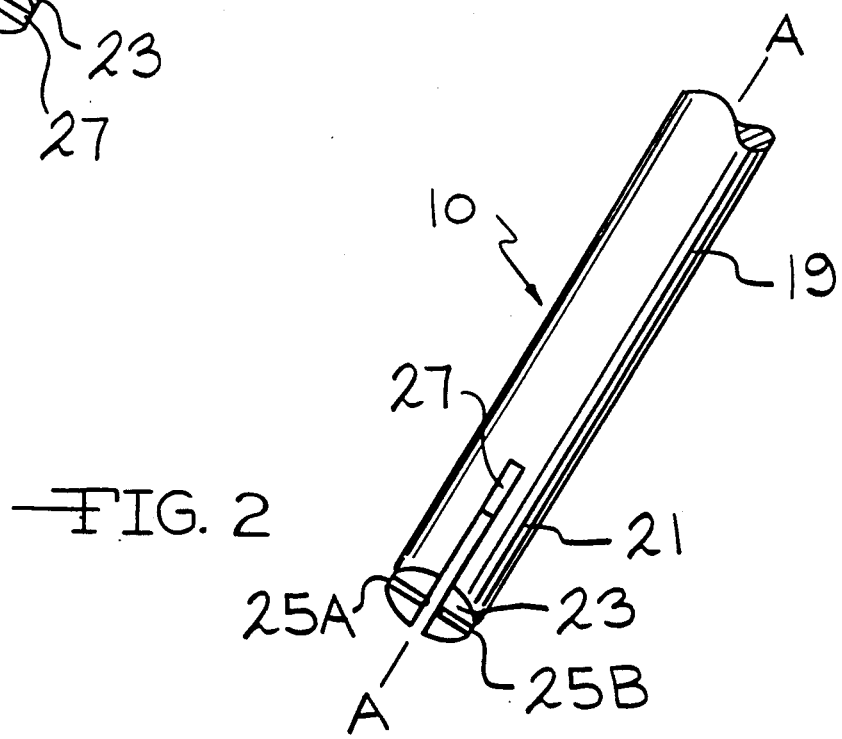
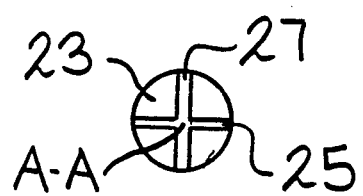

METHOD AND DEVICE FOR SUTURING USING A ROD WITH A NEEDLE HOLDER

BACKGROUND OF THE INVENTION (1) Field of the Invention

The present invention relates to a surgical instrument and a method of using the instrument for tying surgical knots to close an incision or wound in body tissue. In particular, the present invention relates to an elongate instrument that in conjunction with surgical forceps is used to tie suture knots during surgical procedures that are performed inside the body in areas of limited access. Medical procedures that do not require the body part being repaired to be completely opened are being performed with ever increasing frequency. For example, laparoscopy is now frequently used for gallbladder, and other surgeries, operating through small puncture wounds. Because the entry wound that is used to access the surgery area is very small, the cutting and separating of various tissue layers to expose intra abdominal organs is not required. One of the most profound benefits from this type of procedure is that rehabilitation periods are considerably shorter in comparison with traditional fully invasive surgery. During the laparoscopic procedure, the damaged body tissue is repaired by suture knots that must be tied in confined areas inside the abdomen. Often, it is difficult to tie the knots so that they are centered on the incision or wound being repaired. However, it is important that the knots are properly tied to ensure that the tissue sections being joined are drawn together in a uniform manner. This promotes healing by ensuring that the joined tissue will mend with a limited amount of hemorrhaging.

(2) Prior Art

The prior art has described various types of suturing tools used from a remote location outside of the body, to manipulate a needle connected to a length of suture thread, to close a wound or incision inside a body cavity. The prior art suturing tools require that the access opening into the body be only as large as a puncture wound. Surgical tools including the needle and suture are then introduced into the body cavity through the puncture wound to perform the suturing procedure. However, the limited access into the body cavity provided by the puncture wounds makes it difficult to manipulate the suturing tools to center the suture knot on the wound being closed. Illustrative of the prior art is U.S. Pat. Nos. 3,871,379 to Clarke; 4,597,390 to Mulhollan et al; 4,602,635 to Mulhollan et al and 4,683,885 to Hutterer et al.

Clarke describes three surgical instruments and a method for suturing and ligation. The first instrument is a combined needle and forceps and is comprised of an elongated parallelogram type of linkage, which is suitable for insertion through a first cannula. A needle is mounted on a working end of one of the links. The needle is moveable from a position substantially aligned with the linkage to a position transverse to the linkage. A handle, at an opposite end of the linkage, enables a surgeon to move the needle for sewing sutures inside the body. The second instrument is a combined forceps, suture guide and cutter and has an elongated parallelogram type of linkage, which is suitable for insertion through a second cannula. The working end of the linkage is provided with moveable jaws that can be actuated as forceps. The jaws have an associated groove that serves as a suture guide for receiving a suture. The jaws also have opposed cutting blades for cutting sutures. A third instrument comprises a ligator having an elongated stem with a suture guide at one end for guiding a suture through a cannula. These three instruments enable a surgeon or physician to sew a suture into body tissue located in an area of limited access inside the body while working the combined needle and forceps instrument from a remote location, outside of the body. After the suture is sewn into the body tissue, the suture is pulled out of the body, through one of the cannulas, and a knot is tied in the suture. The knot is then slid down the suture to the body tissue being sewn by the ligator instrument. Finally, the suture thread is cut by the cutter blades of the second instrument to complete a surgical suture. These instruments are particularly adapted for laparoscopic surgical procedures.

Mulhollan et al describes two types of surgical instruments for suturing body tissue from a remote location, outside of the body. U.S. Pat. No. 4,597,390 describes a surgical tool for manipulating a needle that has been set in tissue. The surgical tool comprises a tube with a telescoping rod mounted inside of the tube. The tube and rod have a diametrical slot in one end that forms a bifurcated slot. The tube and rod are relatively rotatable so that slot portions in the tube are moveable in and out of alignment with the slot in the rod. When the slot portions are in alignment, the shank of the needle can be received in the slots, and as the slots are moved out of alignment, the needle is gripped by the side walls of the slots. With the needle gripped by the slots, the surgical tool can be manipulated to begin a stitch through the body tissue. Diametrical holes in the tube and rod are also provided and form a bifurcated passage for gripping the top of the needle. That way, the needle can be pulled through the body tissue to complete the stitch. This surgical tool is not useful for centering a suture knot on an incision. U.S. Pat. No. 4,602,635 describes a remote surgical knot tier tool and method for its use. The knot tier tool can be used to tie a knot in suture thread in a remote manipulation area and for pushing and placing the knot into a surgical site in the body of a human being, or an animal through a puncture wound or other small opening. However, pushing the knot into the body tissue does not ensure that the knot will be evenly centered on the body tissue. Thus, the body tissue may not be pulled together evenly, which tends to retard proper mending of the tissue.

Hutterer et al describes a method for tying a double-looped knot in suture thread using an applicator in combination with an endoscopic tube. The applicator is comprised of a coil connected to a longitudinal passage through a shaft. The applicator has hollow turns connected to the shaft passage for reception of the suture thread. The suture thread is passed through a loop projecting from a radial opening at a distal extremity of the shaft. The thread is then drawn through the shaft passage and fastened to the proximal end of the shaft. Tying the single stitch after piercing the tissue is done by passing the needle axially through the coil and then around the thread and twisting the coil out of the loop formed thereby to form the first half of a knot. The knot is then completed by a second half of the knot, which is tied in the same way. The two halves of the knot are then pulled together. However, it is not certain that the knot will be properly centered on the body tissue being sewn. If not, the two halves of the body tissue may not be brought together properly, which retards the mending process.

Other prior art that is less relevant to the present invention includes U.S. Pat. Nos. 2,416,260 to Karle; 2,689,147 to Smalley; and 2,895,478 to Post.

What is not shown by the prior art is a surgical tool that is useful in surgery procedures for centering a suture knot on a wound in body tissue of limited accessibility and that can be manipulated from an area of accessibility, outside the body. If the body tissue is to mend properly, it is important that the suture knot be centered on the wound to join the tissue together in a uniform manner.

OBJECTS

It is therefore an object of the present invention to provide a surgical tool that aids a surgeon or physician in tying and centering suture knots for closing a wound in body tissue. Further, it is an object of the present invention to provide a surgical tool that in conjunction with surgical forceps, is used to tie sutures inside body cavities having limited access. Still further, it is an object of the present invention to provide a method for closing a wound inside of a body cavity having limited access. Furthermore, it is an object of the present invention to provide a method for closing an wound in a body cavity wherein the surgical sutures used to close the wound are centered so that the tissue on either side of the wound is drawn together in a uniform manner. Finally, it is an object of the present invention to provide a surgical tool for use in tying surgical sutures that is inexpensive to manufacture, easy to manipulate during the surgery procedure and that can be ready sterilized for repeated use. These and other objects will become increasingly apparent by reference to the following description and to the drawings.

IN THE DRAWINGS

FIG. 1 is a perspective view of the knot tier instrument 10 of the present invention and particularly showing a notch 25 and a slot 27 in a proximal end 21 of the tool 10.

FIG. 1A is a perspective view of the knot tier instrument 10 shown in FIG. 1 and particularly showing a magnetized proximal end 21A of the tool 10.

FIG. 2 is a perspective view of the knot tier instrument 10 shown in FIG. 1 and particularly showing the slot 27.

FIG. 3 is of a bottom plan view of the knot tier instrument 10 shown in FIGS. 1 and 2 and showing the notch 25 and slot 27 offset 90° from each other.

Figure 4:
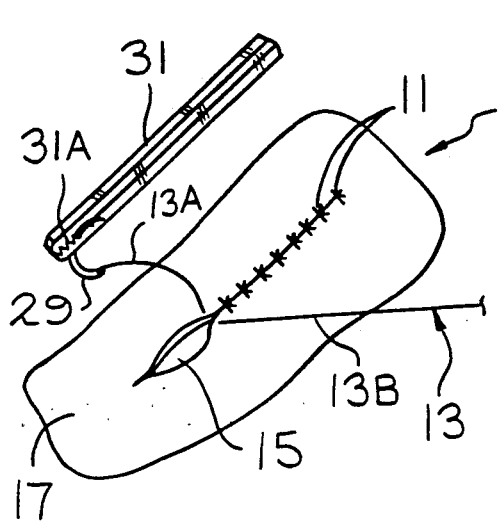

FIG. 4 is a side view of a wound 15 and a pair of elongate forceps 31 holding a needle 29 connected to suture thread 13 for sewing a suture knot 11 in the wound 15.

Figure 5:
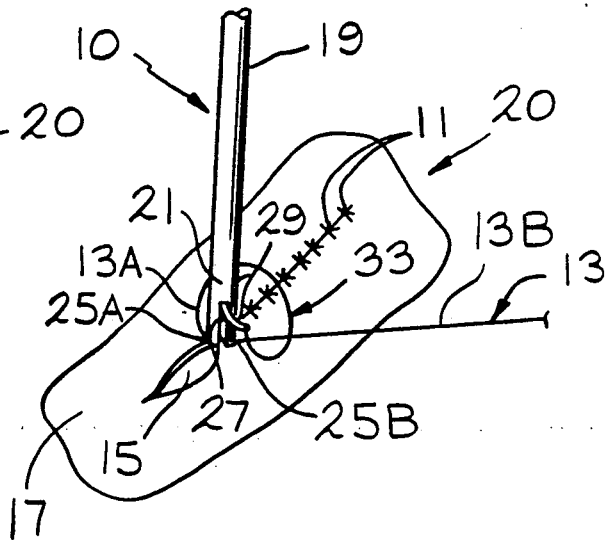

FIG. 5 is a side view of the knot tier instrument 10 shown in FIGS. 1 and 2 with the proximal section 13A of the suture thread 13 looped around the distal section 13B of the suture thread 13 to form a loop 33 and with the needle 29 held in the slot 27.

Figure 6:
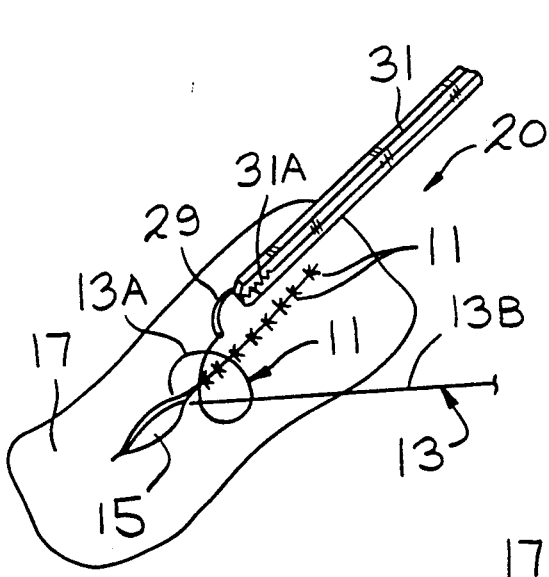

FIG. 6 is a side view of the forceps 31 being used to interlace the proximal and distal sections 13A and 13B of the suture thread 13 to tie a knot 11 in the suture thread 13.

Figure 7:
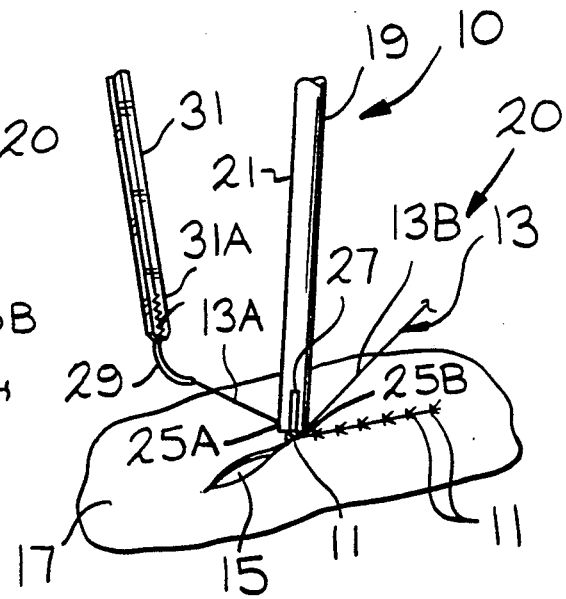

FIG. 7 is a side view of the knot tier instrument 10 mounted on the knot 11 with the proximal and distal sections 13A and 13B of the suture thread 13 positioned on the notch 25 to center the knot 11 on the wound 15.

Figure 8:
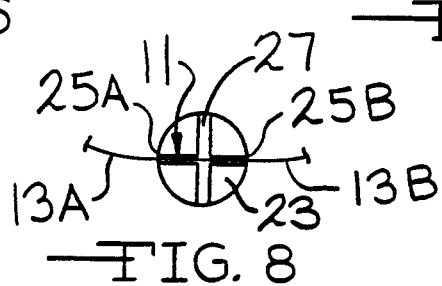

FIG. 8 is a bottom plan view of the surgical knot tier instrument 10 showing the knot 11 positioned in the notch 25.

GENERAL DESCRIPTION

The present invention relates to a surgical instrument for use in conjunction with a driver means and a needle connected to a length of suture thread to close a wound in a body cavity, which comprises: an elongate rod having a first end adapted to be positioned adjacent to the wound and a second end adapted for holding the rod outside of the body cavity, wherein the first end of the rod has a guide means for the suture thread and a holding means adapted to receive and hold the needle connected to the length of suture thread; wherein the driver means is manipulatable to pull the needle through the wound and to form a thread loop at the wound, and with the needle able to be held by the holding means after passing through the wound to provide the loop so that the driver means is releasable from the needle and then the driver means is able to regrasp the needle to pass the needle through the loop in the suture thread to form a knot having a first and second ends extending from the knot and wherein the guide means at the first end of the instrument is positionable on the knot so that the first and second ends of the suture thread are moveable through the guide means to direct the knot towards the wound to tighten the knot and help close the wound.

Further, the present invention relates to a surgical instrument to be used in conjunction with a driver means and a needle connected to a length of suture thread for enabling a wound in a body cavity to be closed, which comprises: an elongate rod having a first end to be positioned adjacent to the wound and a second end adapted for holding the instrument outside of the cavity, wherein the first end of the rod has a guide means for the suture thread and a holding means adapted to receive and hold the needle connected to the suture thread; wherein the driver means is manipulatable for grasping the needle to pull the needle through tissue on both sides of the wound so that the suture thread forms a proximal portion connected to the needle and extending from the wound, and a distal portion extending outside of the cavity from the wound, and wherein the driver means with the needle connected to the proximal portion of suture thread, can be looped around the distal portion of the suture thread and received by the holding means in the first end of the rod to hold the needle, and wherein the needle can then be released by the driver means so that the driver means can be moved around and through the loop to grasp the needle so that the driver means with the needle can be moved back through the loop to form a knot in the suture thread adjacent to the wound and wherein the guide means at the first end of the rod can be positioned over the wound with the proximal portion of the suture thread able to be tensioned to extend through a first end of the guide means and with the distal portion of the suture thread able to be tensioned to extend through a second end of the guide means, wherein the rod can be moved towards the wound with the proximal and distal portions of the suture thread able to be moved through the respective first and second ends of the guide means to direct the knot towards the wound to tighten the knot and to help close the wound.

Finally, the present invention relates to a method of closing a wound in a body cavity, which comprises the steps of: providing a needle connected to suture thread and a surgical instrument which comprises an elongate rod having a first end positioned adjacent to the wound and a second end adapted for holding the rod outside of the body cavity, wherein the first end of the rod has a guide means for the suture thread and a holding means adapted for receiving and holding the needle connected to the suture thread; providing a driver means for grasping the needle and manipulating the driver means to pull the needle through tissue on both sides of the wound so that the suture thread forms a proximal portion connected to the needle and extending from the wound, and a distal portion extending from the wound to outside the body cavity; manipulating the driver means to loop the needle connected to the proximal portion of suture thread around the distal portion of the suture thread and to insert the needle into the holding means in the first end of the rod to hold the needle connected to the proximal portion of the suture thread; releasing the driver means from the needle and moving the driver means around and through the loop formed in the proximal portion of the suture thread and then grasping the needle from the holding means and moving the driver means with the needle connected to the proximal portion of the suture thread back through the loop, thereby forming a knot in the proximal and distal portions of the suture thread adjacent the wound; positioning the first end of the rod over the wound with the proximal portion of the suture thread, which is connected to the needle, tensioned by the driver means holding the needle to extend through a first end of the guide means and with the distal portion of the suture thread tensioned from outside the body cavity to extend through a second end of the guide means; and moving the rod towards the wound with the proximal and distal portions of the suture thread moving through the respective first and second ends of the guide means so that the guide means directs the knot towards the wound to tighten the knot and to help close the wound.

The surgical instrument can be disposed of after the surgical procedure or the instrument can be sterilized and reused. Disposing of the surgical instrument is preferred because it eliminates the possibility of pathogenic or disease causing organisms being transferred from one patient to another. If the surgical instrument is to be reused, it can be sterilized with steam, ethylene oxide or other methods known to those skilled in the art.

DESCRIPTION

FIGS. 1 to 3 show the remote surgical knot tier instrument 10 of the present invention, which is useful in centering a knot 11 tied in suture thread 13 on a wound 15 in body tissue 17 in surgical procedures, whether the surgical procedure is performed on humans or animals. The knot tier instrument 10 is particularly useful when the surgical procedure is to be performed in a body area of limited accessibility, such as is done during an arthroscopic or laparoscopic surgical procedure. An arthroscopic or laparoscopic surgical procedure is considerably more advantageous in comparison to a fully invasive surgical procedure in that the surgery can be performed with greater accuracy, the patient experiences less pain, has a smaller scar, and shorter hospital stay. Also, the rehabilitation period is not nearly as prolonged as that required after a fully invasive surgical procedure.

As shown in FIGS. 1 to 3, the knot tier instrument 10 is comprised of a cylindrically shaped rod member 19 having a proximal, working end 21 and a distal, handle end, (not shown) along a longitudinal axis A—A of the rod member 19. The length of the knot tier instrument 10 along the axis A—A is preferably between about 40 and 50 cm and the diameter is preferably about 0.45 cm to 0.55 cm. The handle enables the knot tier instrument 10 to be held in an area of accessibility, preferably remote from the surgery area and outside of the body. As shown in FIGS. 4 to 7, the proximal end 21 serves as the working end, and in use is positioned adjacent a surgery site 20 in a body. That way, the knot tier instrument 10 can be manipulated by the surgeon or physician as an aid in sewing surgical sutures to close the wound 15 in the body tissue 17. As shown in FIG. 1A, a proximal end 21A of the knot tier instrument 10 can also be made of a metal material that has been magnetized. The term "wound" is used to represent both a surgically made incision in body tissue 25 and a tear in body tissue 25 caused when the body tissue 25 is subjected to a sudden and traumatic damaging force.

As shown in perspective in FIGS. 1 and 2, and in a bottom plan view in FIG. 3, the proximal end 21 of the knot tier instrument 10 is provided with a face 23 having a planar surface, aligned perpendicular to the axis A—A. A notch 25 is cut diametrically across the face 23. The notch 25 is a channel shaped groove having a first end 25A and a second end 25B at the outer periphery of the cylindrical rod member 19. As explained hereinafter, the first and second ends 25A and 25B of the notch 25 serve as guides for receiving first and second sections 13A and 13B of suture thread 13 (FIGS. 4 to 8), to help position the knot 11 tied in the suture thread 13 onto the wound or incision 15 in the body tissue 17 for closing the wound 15. Notch 25 preferably extends to a depth of between about 0.1 and 0.2 cm along the axis A—A. Also, the notch 25 preferably has a width of between about 0.05 and 0.2 cm, along a plane perpendicular to the axis A—A.

The knot tier tool 10 is further provided with a needle receiving slot 27, cut longitudinally along the proximal end 21. Slot 27 is provided diametrically across the face 23, preferably offset 90° from the notch 25. The longitudinal depth of the slot 27 is preferably between about 1 and 1.5 cm. Also, as shown in bottom plan view in FIG. 3, the slot 27 preferably has a width of between about 0.1 and 0.2 cm along a plane perpendicular to the axis A—A. The width of the slot 27 is preferably somewhat wider than the width of the notch 25. The slot 27 serves as a holding means for holding a surgical needle 29 (FIG. 5. As shown in FIG. 1A, a proximal end 21A of the knot tier instrument 10 can also be made of a magnetized metal material, which is preferred. That way, the slot 27 can serve to magnetically hold the needle 29 without a risk that the needle 29 will fall out of the slot 27.

IN USE

During the surgery procedure, a plurality of hollow cannulas or access tubes (not shown), which are well known to those skilled in the art, can be inserted through the skin to help position surgical instruments adjacent to the surgery site 20. It should be understood that the cannulas are not required; however, they are advantageous because they help maintain an airtight seal (pneumoperitoneum) during the surgical procedure. Thus, the knot tier 10 is preferably inserted into a body cavity (not shown) through a first cannula (not shown), which has been positioned through an access incision in the body with the proximal or working end 21 positioned adjacent to the wound 15.

Closing a wound 15 in body tissue 17, located in a body cavity, also requires the use of an elongate forceps instrument 31 and a laparoscope (not shown). The forceps 31 are inserted into the body cavity through a second cannula (not shown) and serve as a driver means for manipulating the needle 29. The laparoscope has a light and an optic probe and is inserted into the body cavity through a third cannula (not shown). The laparoscope is used by the surgeon or physician for viewing the surgical area on a viewing lens or screen, without requiring that the body be surgically opened to expose the surgery area.

As shown in FIG. 4, the forceps 31 have cooperating jaws 31A that provide for gripping and holding the surgical needle 29 connected to the suture thread 13. During the suturing procedure, the suture thread 13 is held taut from an area outside the body while the forceps 31 are used to stitch the needle 29 through the body tissue 17 on both sides of the wound 15. The suture thread 13 is thus formed into the proximal section 13A extending between the wound 15 and the needle 29, and a distal section 13B extending from outside the body to the wound 15.

As shown in FIG. 5, the proximal end 21 of the knot tier instrument 10 is then moved over the wound 15. In this position, the distal section 13B of the suture thread 13, is held taut in the second end 25B of the notch 25 and the proximal section 13A of the suture thread 13 extends through the first end 25A of the notch 25 to the needle 29, held by the forceps 31. The forceps 31 are manipulated to draw the needle 29 around the distal section 13B of the suture thread 13 so that the proximal section 13A of the suture thread 13 forms a loop 33 around the distal section 13B. The forceps 31 are then manipulated to insert and wedge the needle 29 into the slot 27 in the proximal end 21 of the knot tier instrument 10. The needle 29 is held in the slot 27 by being wedged into the slot 27. As shown in FIG. 1A, the proximal end 21A of the knot tier instrument 10 can also be magnetized, which is preferred. In this case, the needle 29 is magnetically held in the slot 27 so that the forceps 31 can be released from the needle 29 without losing the loop 33.

The forceps 31 are then released from the needle 29, held in the slot 27 in the knot tier instrument 10, and manipulated around and behind the loop 33. In that position, the forceps 31 are able to be moved back through the loop 33 to again grasp the needle 29 held in the slot 27. The forceps 31 are then used to remove the needle 29 from the slot 27. As shown in FIG. 6, once the needle 29 is again held securely in the jaws 31A of the forceps 31, the needle 29 is moved through the loop 33 to interlace the proximal and distal sections 13A and 13B of the suture thread 13 to form the knot 11.

The forceps 31 and the knot tier instrument 10 are next used to draw the knot 11 taut against the wound 15 in the body tissue 17 to help close the wound 15. To do this, the forceps 31 are manipulated to position the needle 29, with the proximal section 13A of the suture thread 13 extending away from the wound 15 in a direction opposite the distal section 13B of the suture thread 13. While the suture thread 13 is held in this position, the knot tier instrument 10 is manipulated over the wound 15 and moved into contact with both the proximal and distal sections 13A and 13B of the suture thread 13.

As shown in FIG. 7, the suture thread 13 is then aligned in the notch 25 with the proximal section 13A of the suture thread 13 passing through the first end 25A of the notch 25 and the distal section 13B passing through the second end 25B of the notch 25. The forceps 31 are then used to gently tug the needle 29, connected to the proximal section 13A of suture thread 13, while the distal section 13B is held taut from outside the body. As this happens, the knot tier instrument 10 is slowly moved towards the wound 15 until the knot tier instrument 10 touches the wound 15. This causes the first and second ends 25A and 25B of the notch 25, to slide over the respective proximal and distal sections 13A and 13B of the suture thread 13 to center the knot 11 onto the wound 15. FIG. 8 shows the knot 11 in the notch 25 after the knot 11 has been tightened on the wound 15. This procedure can be repeated any number of times to ensure a secure knot 11.

The proximal and distal sections 13A and 13B of the suture thread 13 are then cut loose from knot 11 with endoscopic (laparoscopic) scissors (not shown) to complete the knot 11. The above described procedure can be repeated any number of times to sew a sufficient number of knots 11 into the wound 15 to close the wound 15, as partially shown in FIG. 7.

It is intended that the foregoing description be only illustrative of the present invention and that the present invention be limited only by the hereinafter appended claims.

I claim:

1. A surgical instrument, for use with a needle connected to a length of a suture thread and a driver means to close a wound in a body cavity, which comprises:
    an elongate rod having a first end and a second end, wherein the first end has a face that is positioned adjacent to the wound and the second end is for manipulating the rod from a position outside of the body cavity, wherein the face of the rod has a guide means defined by a notch across the face for the suture thread and a holding means defined by a slot across the face and along a side of the rod at a depth substantially greater than a depth of the notch to receive and hold the needle connected to the length of suture thread.

2. The surgical instrument of claim 1 wherein the elongate rod has a circular cross-section along a longitudinal axis of the rod and wherein the face at the first end of the rod has a planar surface, perpendicular to the longitudinal axis of the rod.

3. The surgical instrument of claim 2 wherein the notch extends diametrically across the face at the first end of the rod and wherein the slot is formed diametrically across the face at the first end of the rod, offset at a right angle to the notch.

4. The surgical instrument of claim 3 wherein the notch extends along the axis of the rod to a depth of between about 0.1 and 0.2 cm and the slot extends longitudinally along the axis of the rod to a depth of between about 1 and 1.5 cm.

5. The surgical instrument of claim 1 wherein the first end of the rod is made of a magnetic material that helps to hold the needle in the holding means at the first end of the rod.

6. A surgical instrument, to be used with a needle connected to a length of a suture thread and a driver means thereby enabling a wound in a body cavity to be closed, which comprises:

an elongate rod having a longitudinal axis and a first end to be positioned adjacent to the wound and a second end adapted for manipulating the instrument from a position outside of the cavity, wherein the face of the rod has a guide means defined by a notch across the face for the suture thread and a holding means defined by a slot across the face and along a side of the rod at a depth substantially greater than a depth of the notch to receive and hold the needle connected to the suture thread.

7. The surgical instrument of claim 6 wherein the elongate rod has a circular cross-section along the longitudinal axis of the rod and wherein the face at the first end of the rod has a planar surface, perpendicular to the longitudinal axis of the rod.

8. The surgical instrument of claim 7 wherein the notch, provided on the side of the rod, extends to the face and is positioned diametrically across the face at the first end of the rod and wherein the slot is formed diametrically across the face at the first end of the rod, offset at a right angle to the notch.

9. The surgical instrument of claim 8 wherein the notch extends along the axis of the rod to a depth of between about 0.1 and 0.2 cm and the slot extends longitudinally along the axis of the rod to a depth of between about 1 and 1.5 cm.

10. The surgical instrument of claim 6 wherein the first end of the rod is made of a magnetic material that helps to hold the needle in the holding means at the first end of the rod.

11. A method of closing a wound in a body cavity, which comprises the steps of:
(a) providing a needle connected to suture thread and a surgical instrument which comprises an elongate rod having a first end positioned adjacent to the wound and a second end adapted for holding the rod outside of the body cavity, wherein the first end of the rod has a guide means for the suture thread and a holding means adapted for receiving and holding the needle connected to the suture thread;
(b) providing a driver means for grasping the needle and manipulating the driver means to pull the needle through tissue on both sides of the wound so that the suture thread forms a proximal portion connected to the needle and extending form the wound, and a distal portion extending from the wound to outside the body cavity;
(c) manipulating the driver means to loop the needle connected to the proximal portion of suture thread around the distal portion of the suture thread and to insert the needle into the holding means in the first end of the rod to hold the needle connected to the proximal portion of the suture thread;
(d) releasing the driver means from the needle and moving the driver means around and through the loop formed in the proximal portion of the suture thread to enter the loop from a rearward direction and then grasping the needle from the holding means and moving the driver means with the needle connected to the proximal portion of the suture thread forward through the loop, thereby forming a knot in the proximal and distal portions of the suture thread adjacent the wound;
(e) positioning the first end of the rod over the wound with the proximal portion of the suture thread, which is connected to the needle, tensioned by the driver means holding the needle to extend through a first end of the guide means and wit the distal portion of the suture thread tensioned from outside the body cavity to extend through a second end of the guide means, and
(f) moving the rod towards the wound with the proximal and distal portions of the suture thread moving through the respective first and second ends of the guide means so that the guide means directs the knot towards the wound to tighten the knot and to help close the wound.

12. The method of claim 11 wherein the elongate rod has a face at the first end of the rod that provides for a notch as the guide means and wherein a slot, which serves as the holding means is provided on a side of the rod, adjacent the first end of the rod.

13. The method of claim 11 wherein the first end of the rod is made of a magnetic material that helps to hold the needle in the holding means at the first end of the rod.

* * * * *

UNITED STATES PATENT AND TRADEMARK OFFICE
CERTIFICATE OF CORRECTION

PATENT NO. : 5,201,744
DATED : April 13, 1993
INVENTOR(S) : Mark W. Jones

It is certified that error appears in the above-indentified patent and that said Letters Patent is hereby corrected as shown below:

Column 10, line 2, (Claim 11), "form" should be --from--.

Column 10, line 25, (Claim 11), "wit" should be --with--.

Signed and Sealed this

Fourth Day of January, 1994

Attest:

BRUCE LEHMAN

Attesting Officer

*Commissioner of Patents and Trademarks*